US00PP16621P2

(12) United States Plant Patent
Smith

(10) Patent No.: US PP16,621 P2
(45) Date of Patent: Jun. 6, 2006

(54) PLUM CULTIVAR NAMED 'LYDECKER PLUM'

(50) Latin Name: *(Prunus salicina Lindl.×P. besseyi Bailey)×P. salicina L.*
Varietal Denomination: Lydecker

(75) Inventor: Brian R. Smith, River Falls, WI (US)

(73) Assignee: WiSys Technology Foundation, Inc., Madison, WI (US)

( * ) Notice: Subject to any disclaimer, the term of this patent is extended or adjusted under 35 U.S.C. 154(b) by 98 days.

(21) Appl. No.: 10/927,867

(22) Filed: Aug. 27, 2004

Related U.S. Application Data

(60) Provisional application No. 60/499,234, filed on Aug. 29, 2003.

(51) Int. Cl.
*A01H 5/00* (2006.01)

(52) U.S. Cl. ..... Plt./184

(58) Field of Classification Search ..... Plt./184
See application file for complete search history.

(56) References Cited

PUBLICATIONS

Gallagher, Kathleen. "A real plum for Wisconsin growers" Milwaukee Journal Sentinel JSOnline. May 21, 2005. available at: http://www.jsonline.com/news/state/may05/327954.asp.*

* cited by examiner

*Primary Examiner*—Kent Bell
*Assistant Examiner*—W. C. Haas
(74) *Attorney, Agent, or Firm*—Patterson, Thuente, Skaar & Christensen, P.A.

(57) ABSTRACT

A new and distinct cultivar of plum, similar to a Japanese-American hybrid-type originating as a hybrid seedling of the cross: 'Oka'×'Z's Blue Giant'. The present cultivar is unique from its maternal parent and other plums adapted to the Midwest Zone 3b and above, because it is similar to many California dessert plums (dark blue-black and nearly round) and with a superior ripe flavor to most common cultivars tested in its ripening season. The instant cultivar is also more dwarf in growth habit and has an earlier fruit maturity than most common midwest plums.

19 Drawing Sheets

Latin name of the genus and species of the plant claimed: Hybrid of the cross (*Prunus salicina* Lindl.×*P. besseyi* Bailey)×*P. salicina* L.

Cultivar denomination: 'Lydecker'.

BACKGROUND OF THE INVENTION

1. Field of the Invention

The present invention relates to a new and distinctive, plum cultivar advantageously combining desirable characteristics of Japanese and native plum species and which is adapted to northern latitudes.

2. Background

Plums are a desirable fruit for fresh consumption or for use in cooking and baking, being suitable for canning, freezing, and being preserved in jams and jellies. Plums are typically borne on small to medium-sized trees having ovate or elliptic leaves with acute or obtuse tips and short petioles. The flowers of plum trees are similar to those of peaches, but are white, smaller, and have longer pedicels. The lateral and lower buds are found primarily on one-year old wood and on two-year and older spurs. The flower buds open to produce a typical few-flowered fascicle. However, in some cases, may flowers (florets) can be produced from a single bud. Plum fruit is classified as a drupe. Relevant classifications of plums include European and Japanese cultivars.

'Lydecker' plum was developed using cherry plum ('Oka') as the female parent. The primary hardy species in cherry plum is *P. besseyi*, the western sand cherry, which can withstand more severe winters and drought and which also ripens generally one month earlier than *P. americana*, a native wild plum commonly used in hybridization. However, *P. besseyi* has more astringent, smaller fruit and is more susceptible to some diseases. Using the cherry plum as the female parent took advantage of potential maternal effects on winter hardiness. Careful selection of a giant-fruited *P. salicina* ('Z's Blue Giant') as the male parent in the cross was required to circumvent the need to backcross to achieve larger fruit size, yet retain earliness and winter hardiness from the maternal parent in the process. The resultant 'Lydecker' plum is 2 to 4 weeks earlier than any other large, quality plum for the Midwest and has performed very well in winter hardiness tests.

SUMMARY OF THE INVENTION

The instant invention provides a new and distinct cultivar similar to a Japanese-American hybrid-type plum, originating as a seedling in the breeding program at River Falls, Wis. The instant cultivar is unique because the fruit thereof is similar in appearance and flavor to many California dessert plums (dark blue-black and nearly round), but the tree is more naturally dwarf and its fruit is earlier maturing than most other good quality common plum cultivars grown in the Midwest with which it has been compared.

The instant cultivar was developed by Brian R. Smith, Ph.D., a plant breeder at River Falls, Wis. By breeding methodology convention, the hybrid was designated 98-95-21-1, because it originally was discovered within a population designated by the Breeding Record Number 95-21. Breeding Record Number 95-21 is a hybrid population of trees resulting from hybridizing the cultivars 'Oka'×'Z's Blue Giant.' The seedling designated 98-95-21-1 was the first seedling chosen for further evaluation from a population of four siblings possessing the same parentage. The orchard location where the seedling 98-95-21-1 was first grown and noticed was designated as Field Number 6, Row 3, Tree 11. The seedling 98-95-21-1 was first noticed because it had fruit similar to its paternal parent, 'Z's Blue Giant.' However, the fruit was borne on a tree more dwarf in growth habit and exhibiting superior winter hardiness, the fruit thereof ripening significantly earlier than those of 'Z's Blue Giant.'

Figure 1:
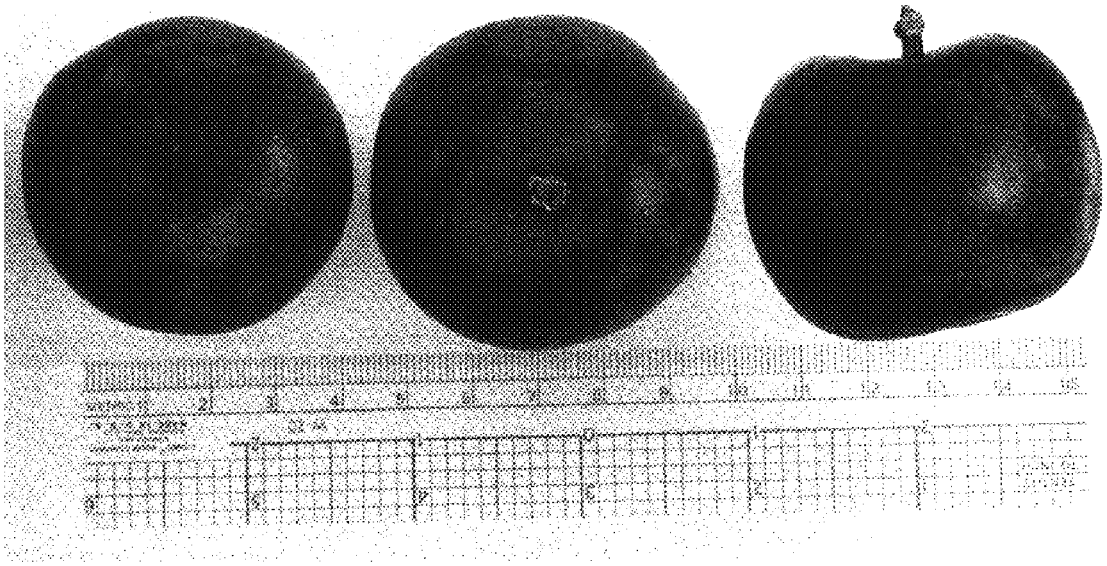
FIG. 1 illustrates the intact fruit of the present cultivar at maturity.
Figure 2:
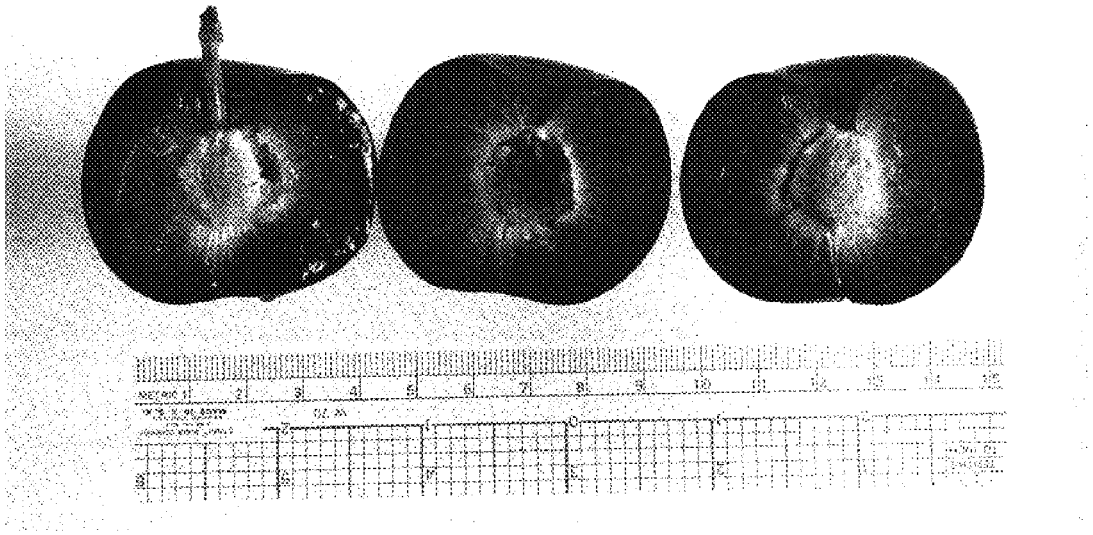
FIG. 2 illustrates one view the fruit halves of the present cultivar as cut at the suture line.
Figure 3:
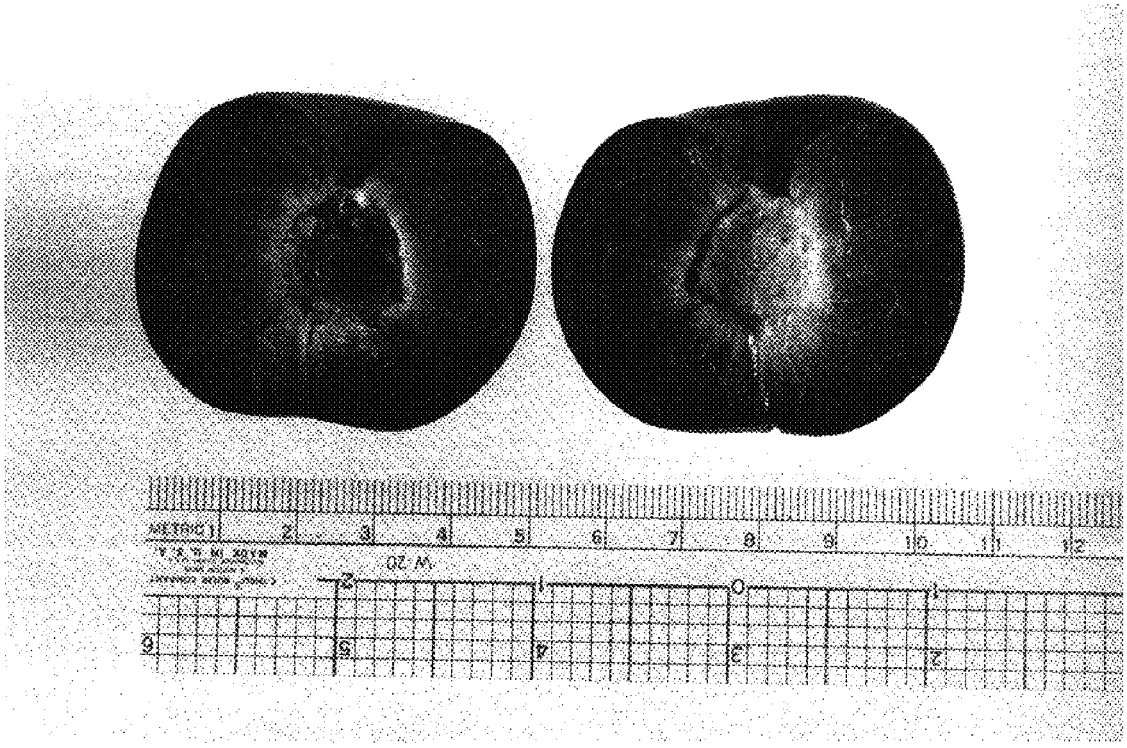
FIG. 3 illustrates another view of the fruit halves of the present cultivar as cut at the suture line.
Figure 4:
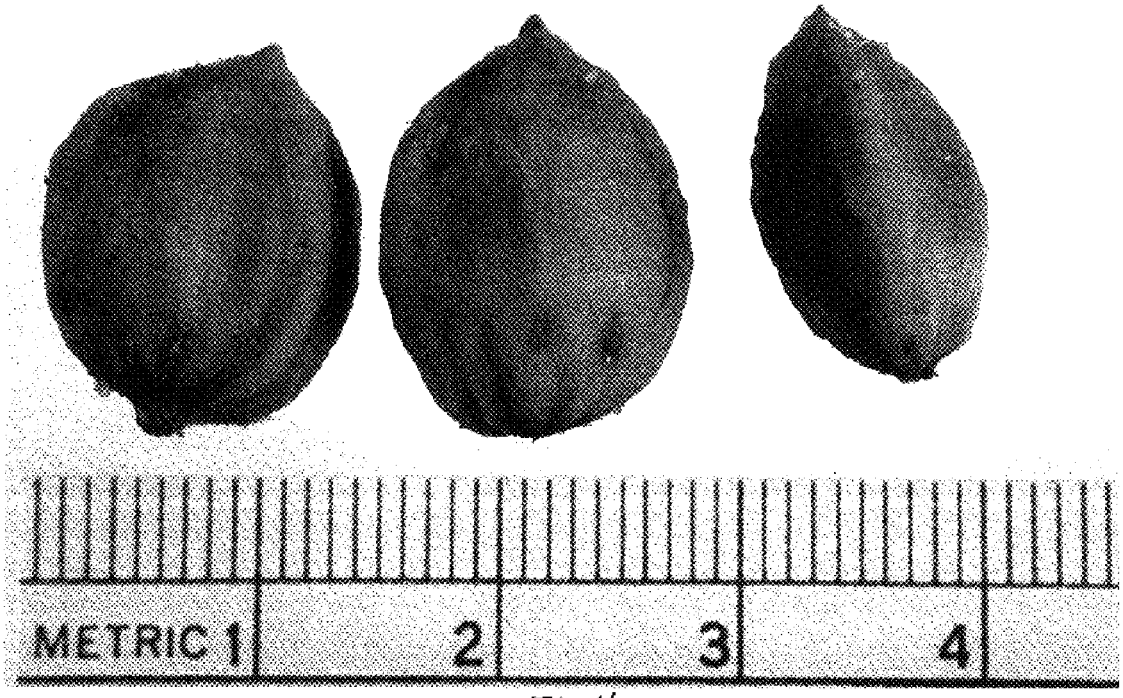
FIG. 4 illustrates the pit (endocarp) of the present cultivar as extracted from the mature fruit.
Figure 5:
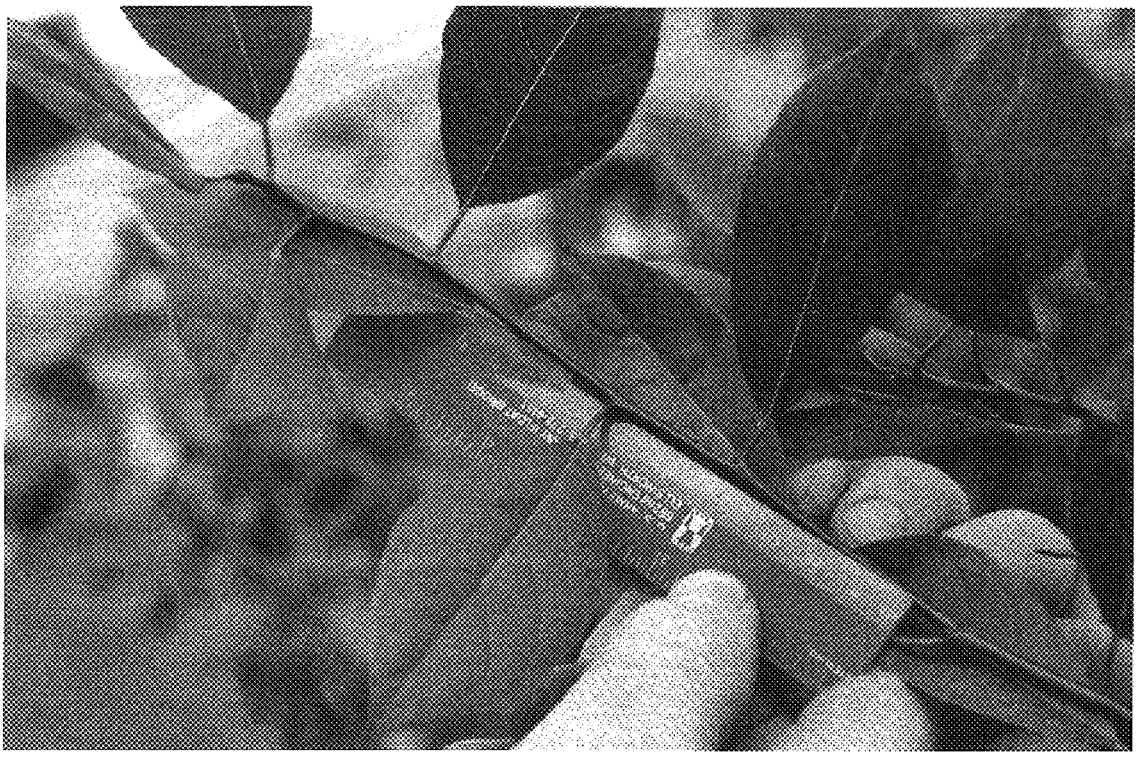
FIG. 5 illustrates a vegetative twig of the present cultivar from the annual, apical growth of a lateral branch in the year 2004.
Figure 6:
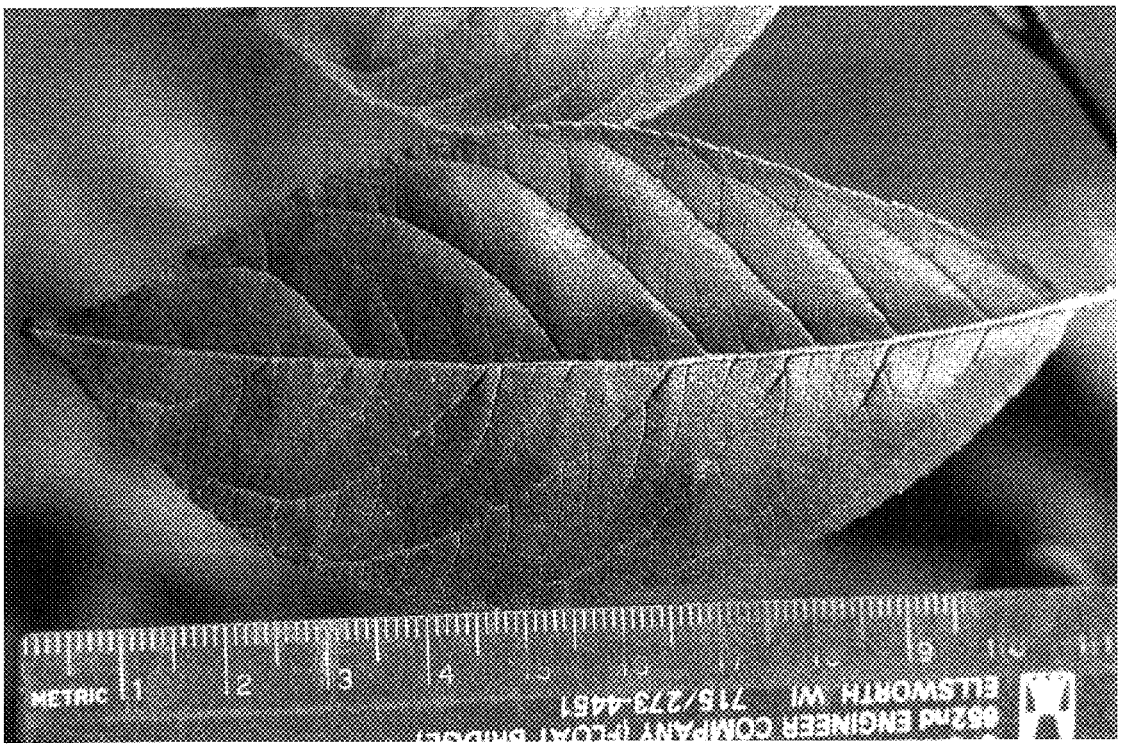
FIG. 6 illustrates one view of the adaxial surface of a leaf of the present cultivar.
Figure 7:
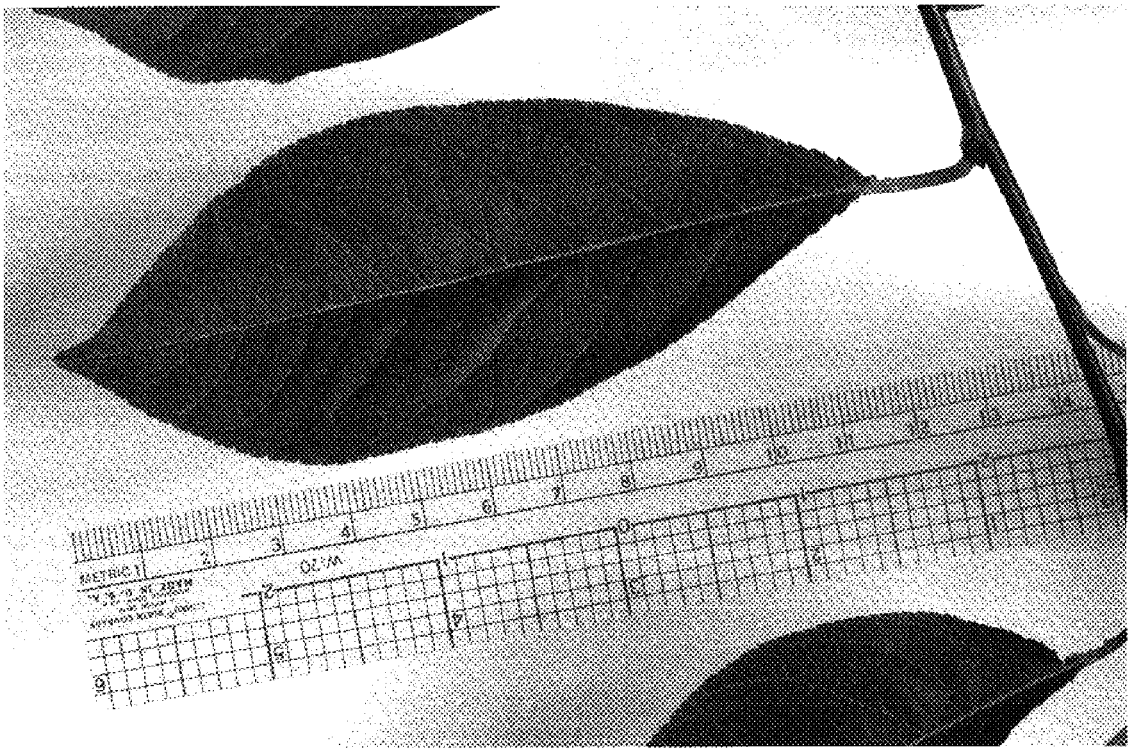
FIG. 7 illustrates another view of the adaxial surface of a leaf of the present cultivar.
Figure 8:
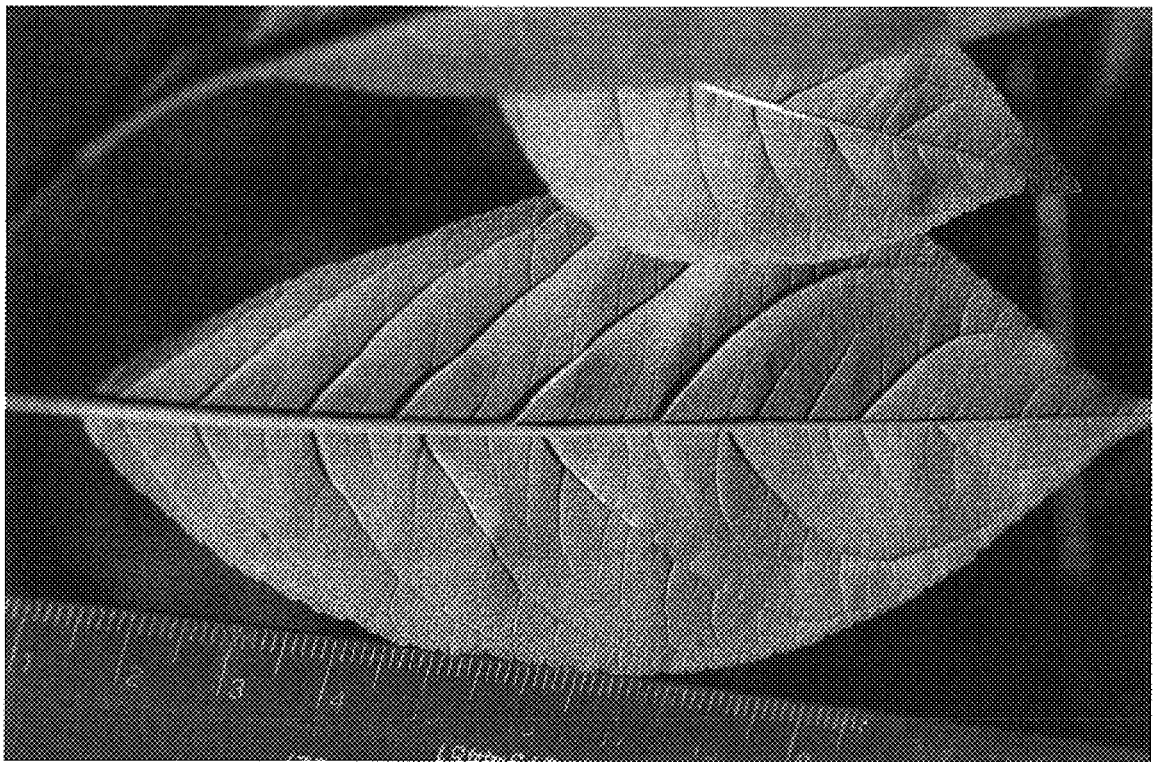
FIG. 8 illustrates one view of the abaxial surface of a leaf of the present cultivar.
Figure 9:
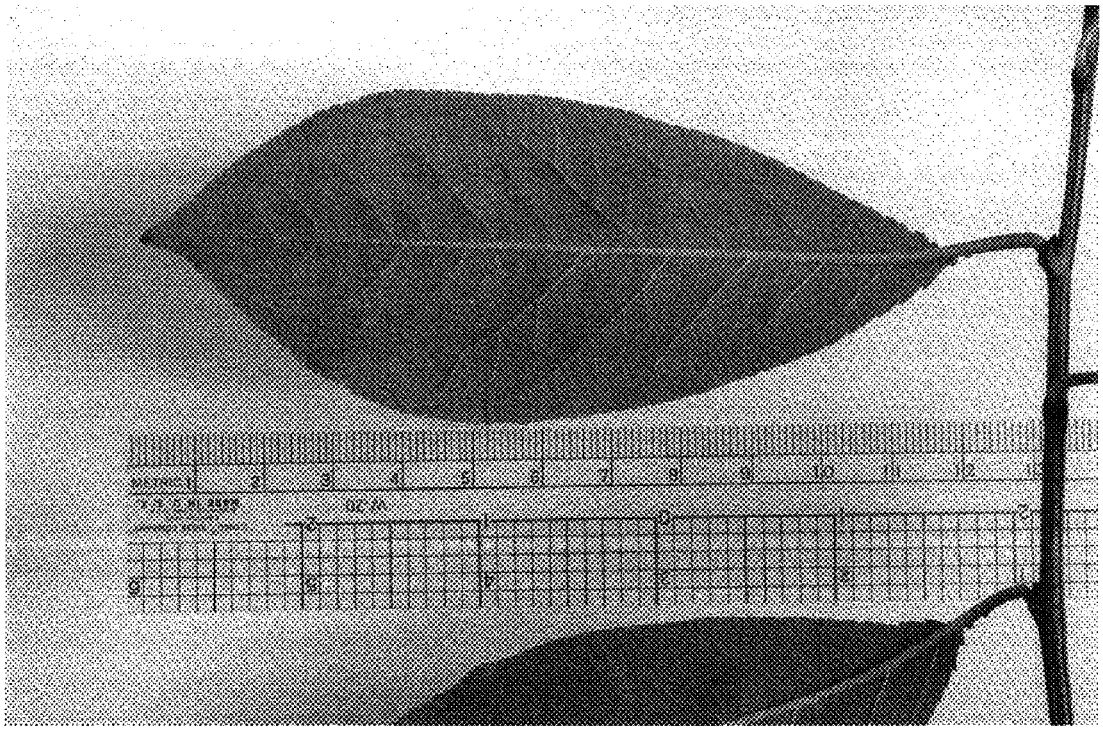
FIG. 9 illustrates another view of the abaxial surface of a leaf of the present cultivar.
Figure 10:
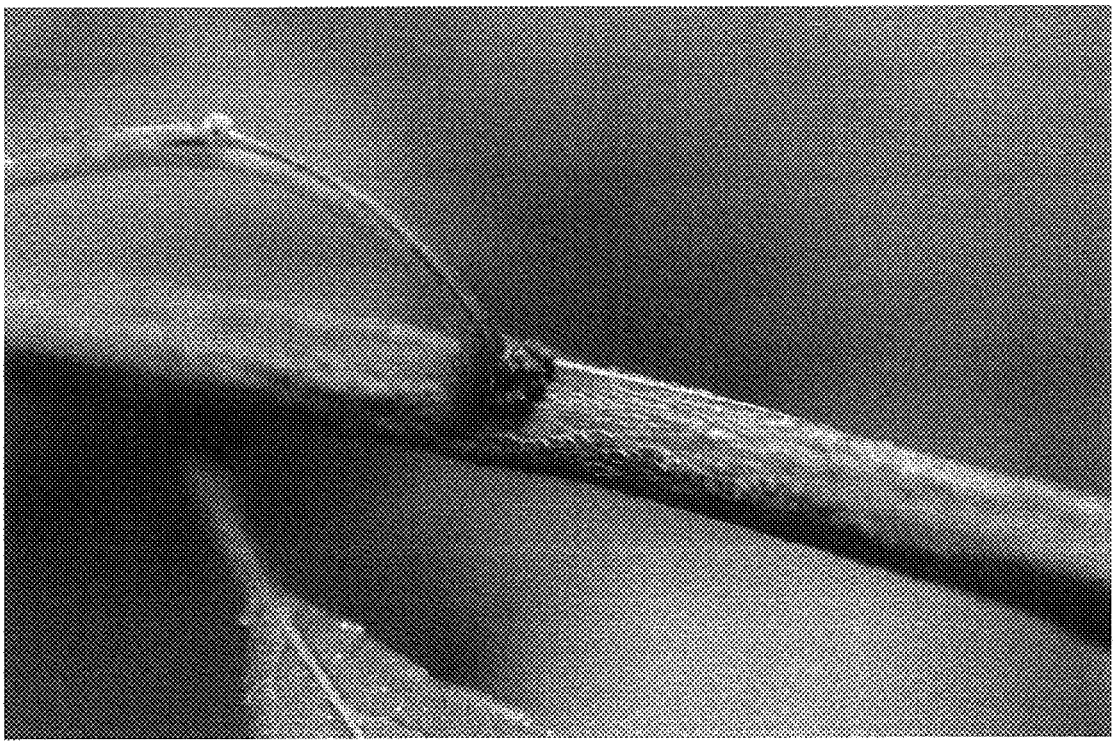
FIG. 10 illustrates one view of both the vegetative and flower buds of the present cultivar in close-up.
Figure 11:
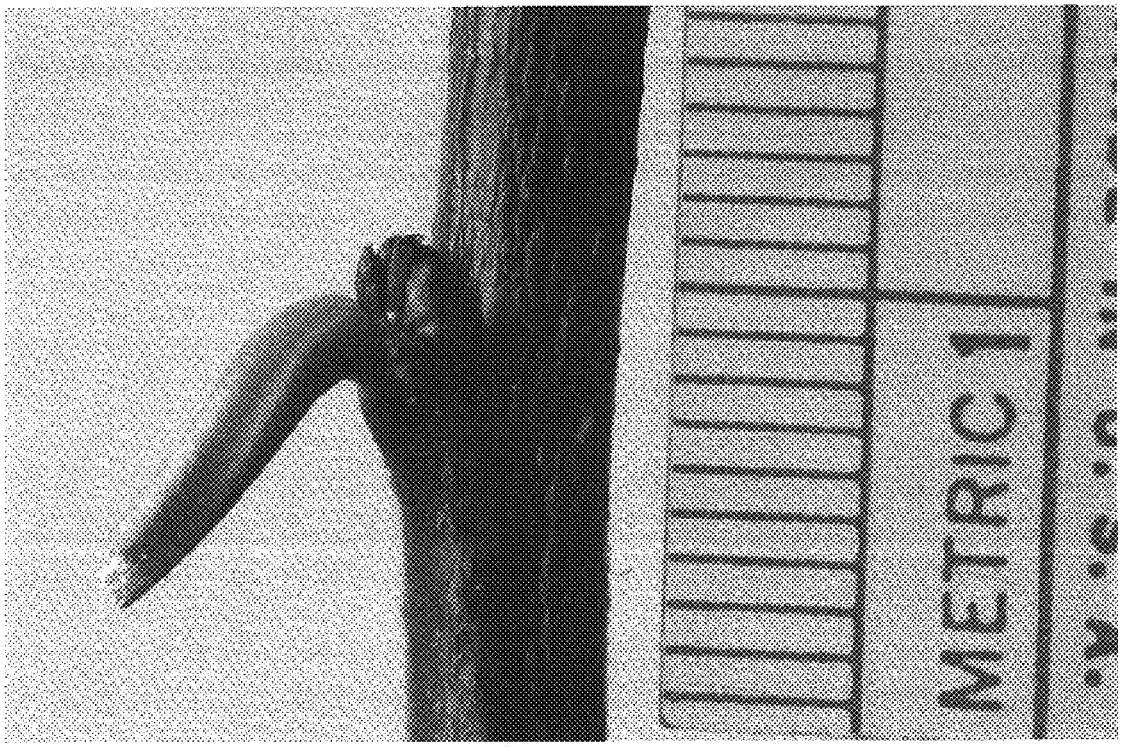
FIG. 11 illustrates another view of both the vegetative and flower buds of the present cultivar in close-up.
Figure 12:
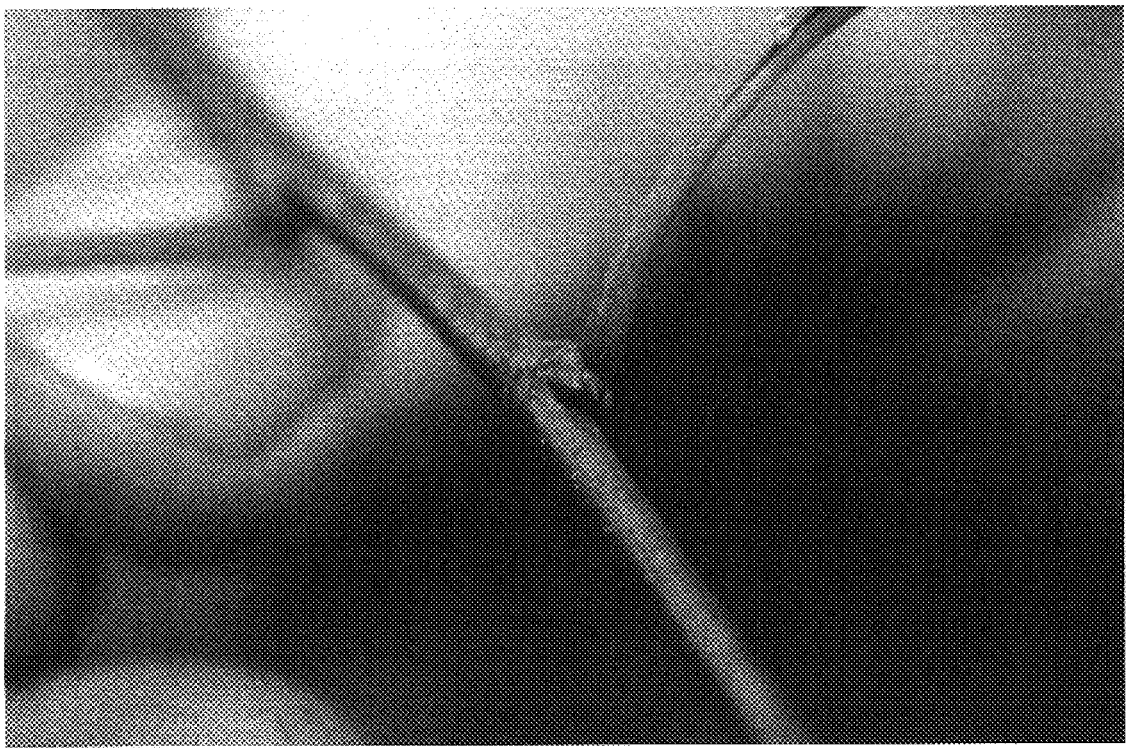
FIG. 12 illustrates yet another view of both the vegetative and flower buds of the present cultivar in close-up.
Figure 13:
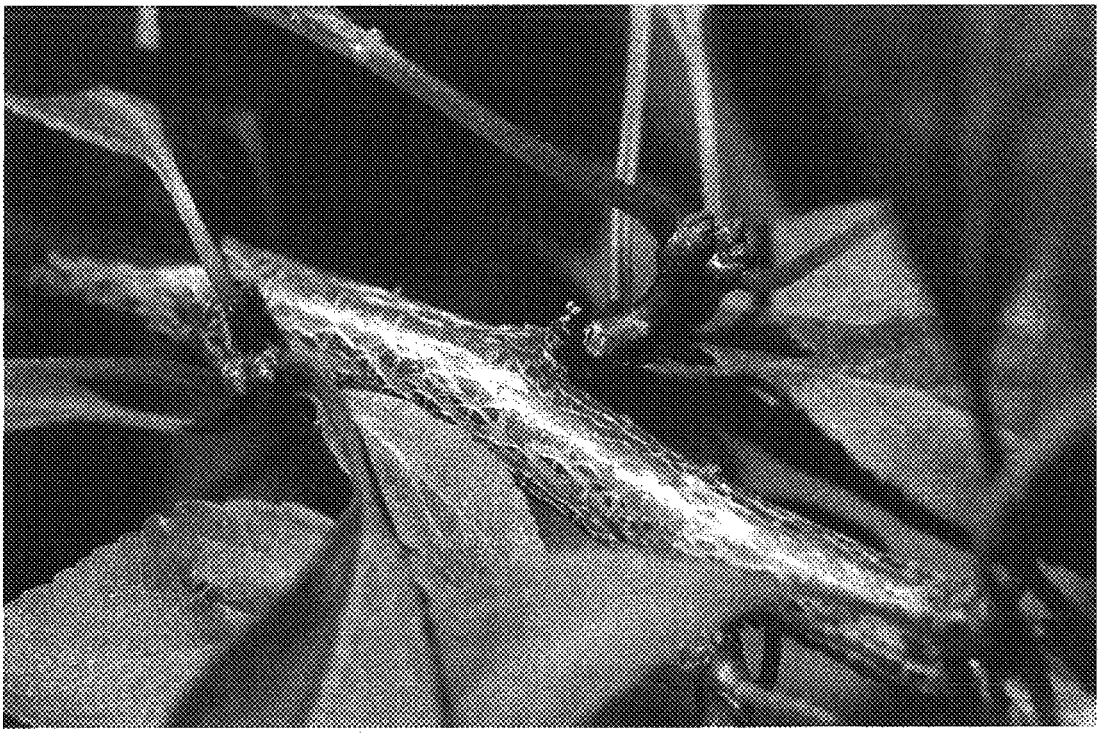
FIG. 13 illustrates one view of the fruit spurs.
Figure 14:
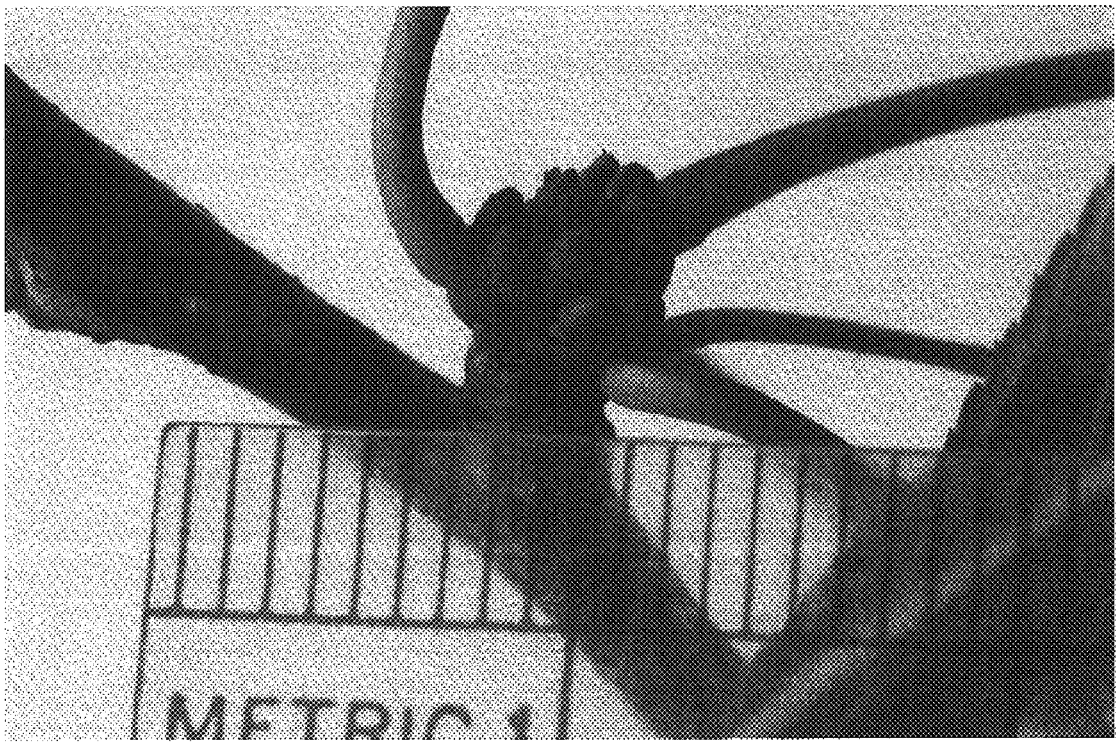
FIG. 14 illustrates another view of the fruit spurs in close-up.
Figure 15:
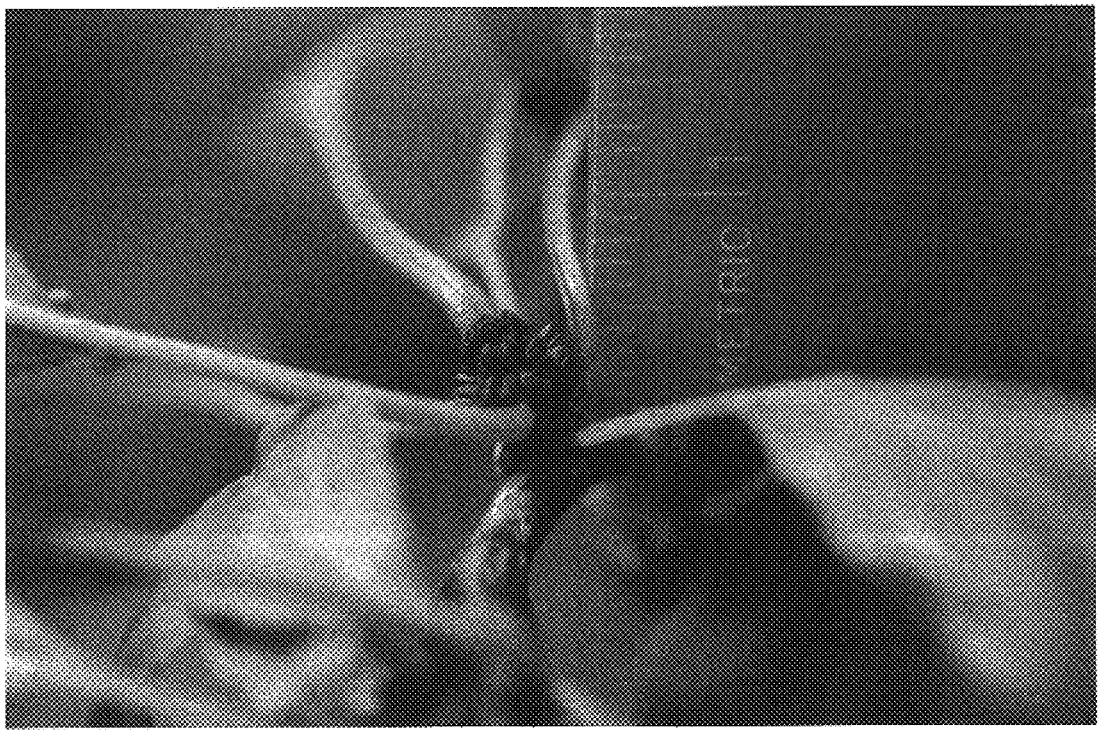
FIG. 15 illustrates yet another view of the fruit spurs in close-up.
Figure 16:
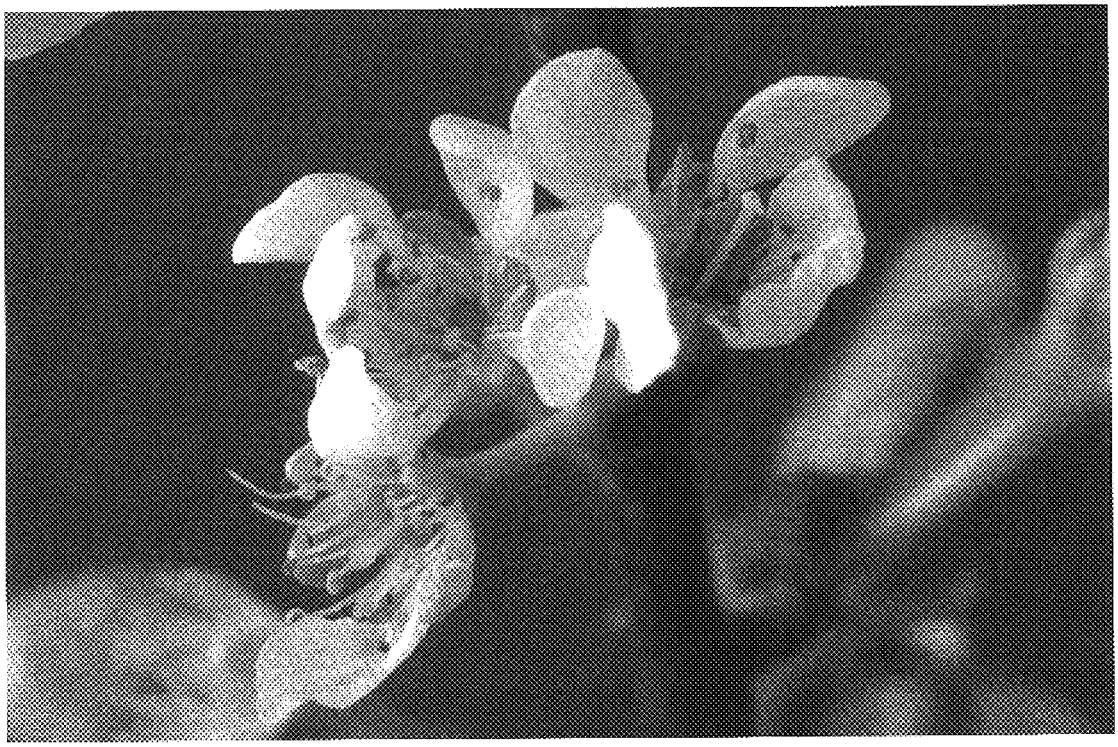
FIG. 16 illustrates one view of the flowers of the present cultivar.
Figure 17:
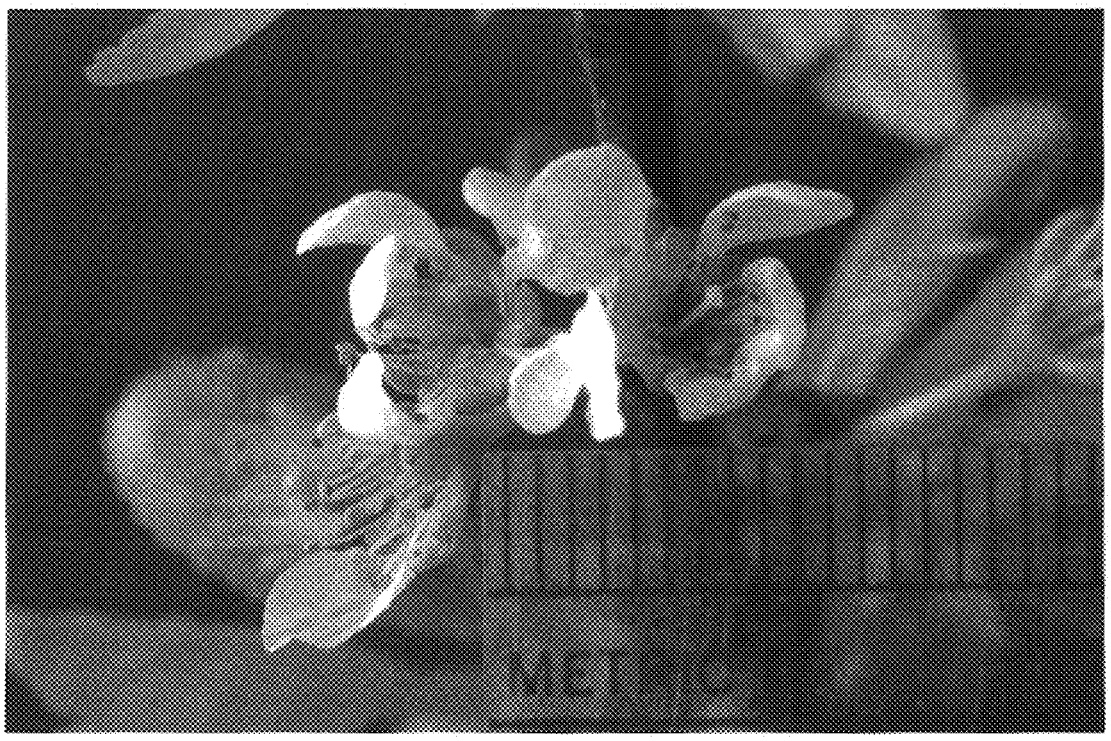
FIG. 17 illustrates another view of the flowers of the present cultivar.
Figure 18:
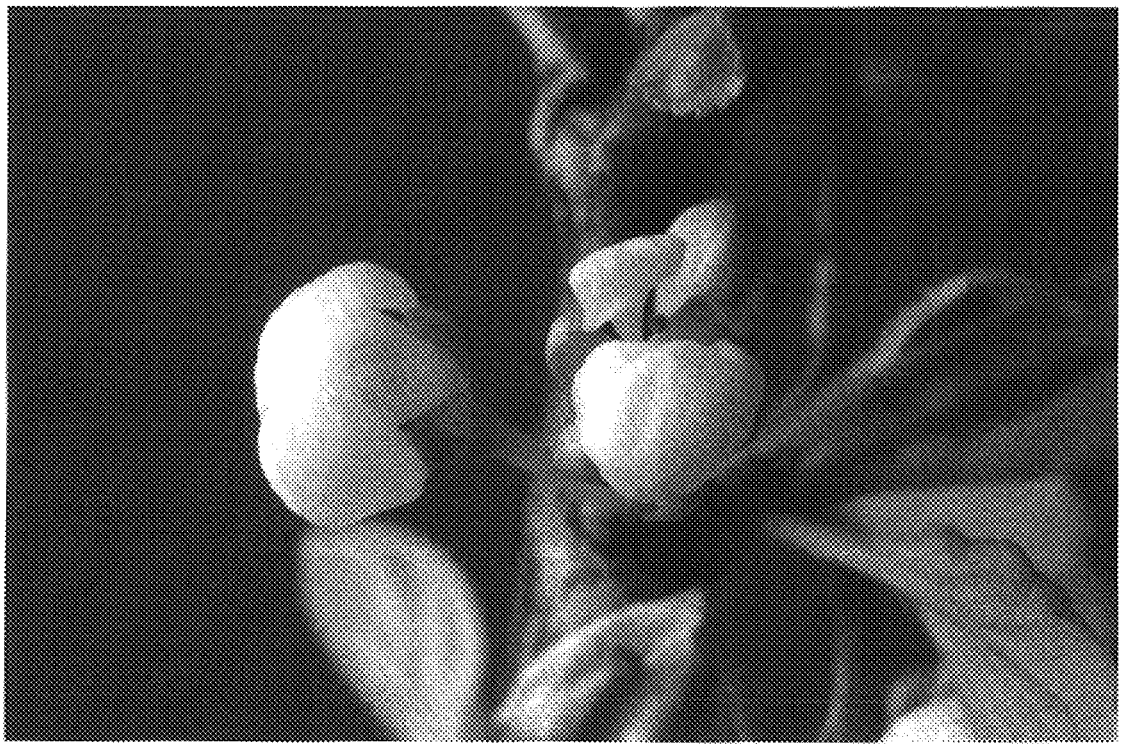
FIG. 18 illustrates yet another view of the flowers of the present cultivar in balloon stage.
Figure 19:
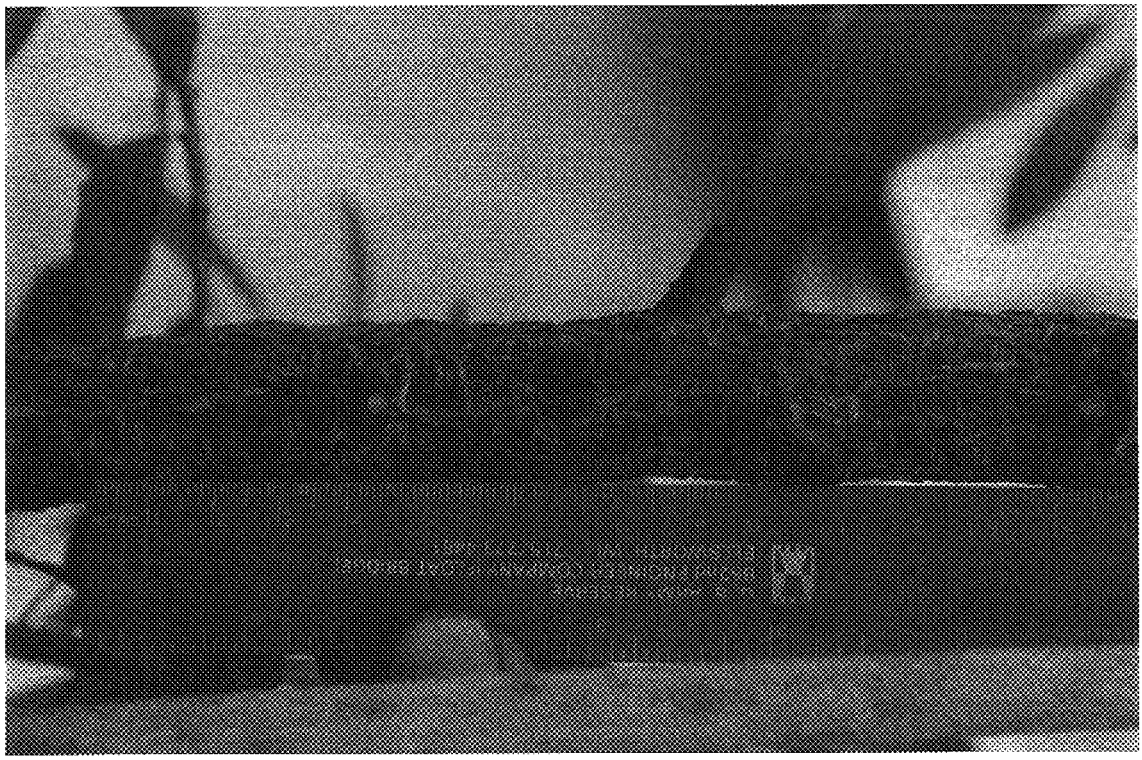
FIG. 19 illustrates a 3 year old limb of the present cultivar.

It is understood that the above-described figures are only illustrative of the present invention and are not contemplated to limit the scope thereof.

BOTANICAL DESCRIPTION OF THE PLANT

The detailed description of an exemplar of the 'Lydecker' Plum cultivar hereinbelow uses The Royal Horticultural Society of London Colour Chart for color identification, except where general color terms are sufficient. Where colors shown in the figures are inconsistent with colors described and stated in the specification, the specification will control.

Parentage: A hybrid seedling of the cross: 'Oka'×'Z's Blue Giant.' Locality of the original discovery and observations is River Falls, Wis., U.S.A. The present plum tree was tested under the designation "98-95-21-1."

Tree:

*Age of specimen.*—9 years old.

*Height.*—2.5 M.

*Width.*—2 M.

*Size.*—Small.

*Vigor.*—Medium.

*Density.*—Medium.

*Form.*—Slightly upright, with medium level of lateral branching.

*Production.*—Heavy at full maturity and precocious.

*Bearing.*—Annual on spurs and one year old shoots.

*Disease resistance.*—Average susceptibility to brown rot (*Monilinia fructicola*) fruit attack but more tolerant than 'Alderman' (unpatented) to shoot and twig attacks. The instant cultivar is considered to be more tolerant to bacterial spot (*Xanthomonas campestris* pv. *Pruni*) than 'Alderman' and 'Superior' (unpatented) and Black knot (*Dibotryon morbosum*) susceptibility appears similar to most Japanese-American Hybrid plums grown in the Midwest.

*Insect resistance.*—Average susceptibility to most common stone fruit insects.

*Cold hardiness.*—Very good, crops regularly in USDA Hardiness Zone 3b.

*Graft compatibility.*—Good, produces compatible graft unions with 'Mariana 2624(unpatented)', Myrobolan Seedlings and *Prunus americana* seedling rootstock.

Trunk:

*Size.*—8 cm in diameter at 15 cm above soil level.

*Surface.*—New bark is smooth with somewhat inconspicuous lenticels, older bark is rough.

*Lenticels.*—Sparse in number, varying in length from 2 mm to 3.5 mm and width from 0.75 mm to 1.0 mm, inconspicuous, horizontal, elliptical, White 155 D.

*Older bark.*—Greyed Purple Group H187 A to Grey Group 201 A.

*Newer bark.*—Greyed Orange 174 A.

*Newest bark.*—Grey Brown N 199 A.

Vegetative buds:

*Placement.*—½–⅔ exposed by base of petiole.

*Appearance.*—Pointed and surrounding bark is non-pubescent.

*Length.*—2 mm.

*Width.*—1 mm at base.

*Color.*—Grayed Orange Group 177 B to Brown Group 200 D.

*Internode length.*—3.2 cm.

*Spur.*—Pointed apical buds at tips of spurs ranging from 3 to 12 buds.

Lamina of leaf:

*Size.*—9 cm to 10.5 cm in length, to 4.5 cm in width.

*Form.*—Elliptic.

*Thickness.*—Medium.

*Margin.*—Very finely serrated with some variable shapes but most are recurved sawtooth.

*Adaxial surface.*—Smooth, but not shiny green, Green Group 139 A.

*Abaxial surface.*—Dull luster to green coloration, Yellow-Green Group 147 B.

*Glands.*—Few, small, oval, color Yellow-Green Group 150 D.

*Anthocyanin coloration.*—59B, apparent on glands and upper ridges of petiole grooves.
*Stipules.*—None observed.

Petiole:
*Size.*—Length 1.75 cm to 2.25 cm, diameter 1.2 mm. Many distinctly recurved as age.
*Color.*—Green Group 137 C with Red Purple Group 59 B on ridges/grooves.
*Surface texture.*—Smooth, glossy with a prominent groove.

Flowers:
*Blooming period.*—Early-mid, April 25 to May 1 in River Falls, Wis.
*Presentation.*—Non-showy.
*Fragrance.*—Faint, sweet, wild plum.
*Fertility.*—Self-sterile.
*Pollen.*—Very little to absent. Will not serve as pollinizer.
*Corolla diameter.*—13 mm.
*Petals.*—Single, 5 in number, not overlapping, oval, length 8 mm, width 4.5 mm, margin very slightly wavy, soft texture, White 155 D.
*Number of flowers per fascicle.*—2 to 4.
*Pedicel.*—14 mm in length, 1 mm in width.
*Pedicel surface texture.*—Smooth.
*Pedicel color.*—Yellow-Green Group 145 B.
*Number of stamens.*—25 to 31.
*Filaments.*—Length 4 mm, width 0.25 mm, White 155 D.
*Anthers.*—Below Corolla, pollen absent, Greyed Orange Group 166 B.
*Style.*—Length 3 mm to 5 mm, color Yellow-Green Group 149 D.
*Stigma.*—Round, diameter 0.5 mm, color Yellow-Green Group 149 D.
*Sepals.*—5 in number, pointed in, rounded, Green 143 C.

Fruit:
*Maturity when described.*—Commercial ripeness, soluble solid content is 14 degrees Brix.
*Date of first picking.*—Early-mid ripening, August 6 at River Falls, Wis.
*Size.*—5.5 cm in length, 5.5 cm in width.
*Form.*—Nearly round, indented on stem end and nearly flat at pistillate end.
*Base.*—Nearly flat with moderate indentation at stem cavity.
*Stem cavity.*—Elliptical, 17 mm across end, 25 mm across suture, medium sized tan dots numerous, uniform.
*Stem scar.*—May develop cracks that extend into connecting suture tissues for up to 4 mm in length under fluctuating environmental conditions.
*Apex.*—Rounded.
*Suture.*—Extends around dorsal surface, smooth, indented from 0.3 mm to 0.6 mm.
*Ventral surface.*—Smooth to very slightly indented at suture.

Skin:
*Thickness.*—Medium.
*Texture.*—Elastic, but not unpleasing.
*Tendency to crack.*—May split on suture adjacent to the stem scar/cavity in high rainfall seasons.
*Bloom.*—Present, and moderate in its graying effect on skin color.
*Flavor.*—Fruity, sweet plum flavor with aromatic essence present.

Flesh:
*Texture.*—Medium firm, juicy.
*Acidity.*—Medium high until sugar level rises about 12 degrees Brix.
*Flavor.*—Excellent, with some aromatic essence present.
*Aroma.*—Present, pleasing.
*Fibers.*—Few.
*Color.*—Purple Group 75 D around part of pit, also Red Group 46 A radiating out to Greyed Purple Group 185 A.
*Eating quality.*—Very good when mature to 14 degrees Brix, slightly acid if eaten when immature.

Pit (endocarp):
*Size.*—17 mm in length, 14 mm in width at widest point.
*Form.*—Ovoid, asymmetrical, widest point at center.
*Apex.*—Narrowing to round tip at style end.
*Sides.*—Slight wing on suture.
*Base.*—Flat to rounded.
*Surface.*—Rough.
*Color.*—Greyed-Orange Group 163 D.
*Type.*—Semifreestone at commercial maturity.
*Tendency to crack.*—Non-existent.

Stem:
*Length.*—Thick, 15 mm in length; 4 mm in width at branch attachment, tapered to 3 mm at pit attachment.
*Color.*—Grey-Brown Group N199 D.
*Texture.*—Very slightly pubescent.

Use: Dessert, for fresh market.

What is claimed is:

1. A new and distinct hybrid plum tree (*Prunus salicina* Lindl.×*P. besseyi* Bailey)×*P. salicina* L., substantially as shown and described herein and characterized by a fruit resembling *P. salicina* Lindl. borne on a substantially dwarf-type tree, with superior winter hardiness and an early ripening date.

* * * * *